(12) United States Patent
Clemens et al.

(10) Patent No.: US 7,973,083 B2
(45) Date of Patent: Jul. 5, 2011

(54) PESTICIDALLY ACTIVE COMPOUNDS

(75) Inventors: Christopher Glen Clemens, Richland, WA (US); Willy Thaddaeus Rueegg, Stein (CH); Michael Joseph Urwiler, Champaign, IL (US)

(73) Assignee: Syngenta Crop Protection LLC, Greensboro, NC (US)

( * ) Notice: Subject to any disclaimer, the term of this patent is extended or adjusted under 35 U.S.C. 154(b) by 741 days.

(21) Appl. No.: 10/580,363

(22) PCT Filed: Nov. 3, 2004

(86) PCT No.: PCT/EP2004/012417
§ 371 (c)(1),
(2), (4) Date: Jan. 29, 2007

(87) PCT Pub. No.: WO2005/053407
PCT Pub. Date: Jun. 16, 2005

(65) Prior Publication Data
US 2008/0058212 A1    Mar. 6, 2008

Related U.S. Application Data

(60) Provisional application No. 60/526,053, filed on Dec. 1, 2003, provisional application No. 60/545,302, filed on Feb. 17, 2004.

(51) Int. Cl.
| | |
|---|---|
| *A01N 33/22* | (2006.01) |
| *A01N 35/04* | (2006.01) |
| *A01N 57/14* | (2006.01) |
| *A01N 57/12* | (2006.01) |
| *A01N 53/06* | (2006.01) |
| *A01N 43/72* | (2006.01) |
| *A61K 31/122* | (2006.01) |
| *A61K 31/675* | (2006.01) |
| *A61K 31/661* | (2006.01) |
| *A61K 31/215* | (2006.01) |
| *A61K 31/5395* | (2006.01) |

(52) U.S. Cl. .......... 514/683; 514/89; 514/144; 514/531; 514/229.2

(58) Field of Classification Search .................. None
See application file for complete search history.

(56) References Cited

U.S. PATENT DOCUMENTS

| 4,230,481 A | 10/1980 | Nishiyama et al. | |
|---|---|---|---|
| 5,695,773 A * | 12/1997 | Schapira et al. | 424/405 |
| 5,741,756 A * | 4/1998 | Shribbs | 504/149 |
| 5,912,207 A * | 6/1999 | Scher et al. | 504/190 |
| 5,962,370 A | 10/1999 | Gamblin et al. | |
| 6,746,988 B2 * | 6/2004 | Hopkinson et al. | 504/127 |
| 2004/0180790 A1 * | 9/2004 | Cornes | 504/133 |
| 2005/0233986 A1 * | 10/2005 | Clough | 514/28 |

FOREIGN PATENT DOCUMENTS

| DE | 2004-012192 A1 | 9/2004 |
|---|---|---|
| WO | WO-01-95722 A1 | 12/2001 |
| WO | WO-2004-082382 A1 | 9/2004 |

* cited by examiner

*Primary Examiner* — Johann R Richter
*Assistant Examiner* — Jessica Kassa
(74) *Attorney, Agent, or Firm* — William A. Teoli, Jr.

(57) ABSTRACT

A pesticidally active combination comprising an HPPD-inhibiting herbicide in the form of an agrochemically acceptable salt and an insecticide is disclosed, provided that the HPPD inhibiting herbicide is not a compound of formula (A) wherein $R^a$ is $C_{1-2}$ alkyl or chloro; $R^b$ is hydrogen or $C_{1-4}$ alkyl; and $R^c$ is $C_{1-4}$ alkyl is disclosed.

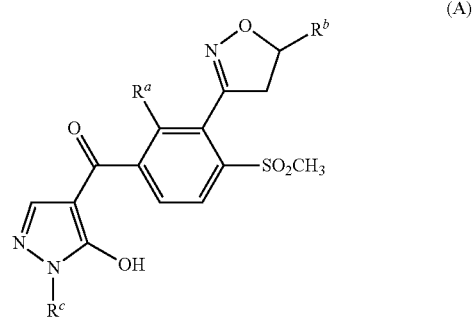

(A)

7 Claims, No Drawings

PESTICIDALLY ACTIVE COMPOUNDS

This application is a 371 of International Application No. PCT/EP2004/012417 filed Nov. 3, 2004, which claims priority to U.S. 60/526,053 filed Dec. 1, 2003, and U.S. 60/545,302 filed Feb. 17, 2004, the contents of which are incorporated herein by reference.

The present invention relates to a novel pesticidally active combination comprising a herbicidally active ingredient in the form of an agrochemically acceptable salt and one or more insecticidally active ingredients, and optionally one or more additional active ingredients. The invention relates also to a method of controlling unwanted growth in crops of useful plants.

The protection of crops from weeds and other pests that inhibits crop growth is a constantly recurring problem in agriculture. To help combat this problem, researchers in the field of synthetic chemistry have produced an extensive variety of chemicals and chemical formulations effective in the control of such unwanted pests. Chemical pesticides of many types have been disclosed in the literature and a large number are in commercial use. Commercial pesticides and some that are still in development are described in The Pesticide Manual 12$^{th}$ Edition, published in 2000 by the British Crop Protection Council.

Agricultural pesticide manufacturers have identified the need for broad-spectrum pesticidally active products. Single active ingredient formulations rarely meet such broad-spectrum requirements, and thus combination products, perhaps containing up to four complementary biologically active ingredients, have been developed. Such products have several additional advantages e.g. elimination of tank mixing; reduction in inventory products; saving in time and money; and a reduction in the number of times the crop is sprayed.

One combination considered was a combination of an HPPD inhibiting herbicide with an insecticide. However, when tested, the crop damage seen was considerably increased, compared to that seen following application of the HPPD inhibiting herbicide alone. It was then surprisingly discovered by the inventors that if an agrochemically acceptable salt of the HPPD inhibitor was used a safening effect was seen and the crop damage caused by the combination was considerably reduced to an acceptable level.

Accordingly, the present invention provides a pesticidally active combination comprising an HPPD-inhibiting herbicide in the form of an agrochemically acceptable salt and an insecticide, provided that the HPPD-inhibiting herbicide is not a compound of formula (A)

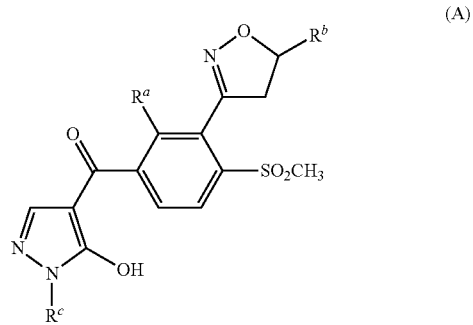

wherein $R^a$ is $C_{1-2}$ alkyl or chloro; $R^b$ is hydrogen or $C_{1-4}$ alkyl; and $R^c$ is $C_{1-4}$ alkyl.

The HPPD-inhibiting herbicides for use in the present invention are suitably selected from the group consisting of isoxazoles, triketones, pyrazoles, benzobicyclon and ketospiradox.

Suitably, the isoxazole is a compound of formula (IA)

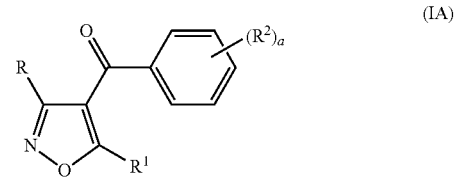

wherein R is hydrogen or —CO$_2$R$^3$;
R$^1$ is C$_{1-4}$ allyl or C$_{3-6}$ cycloalkyl optionally substituted by C$_{1-6}$ alkyl;
R$^2$ is independently selected from halogen, nitro, cyano, C$_{1-4}$ alkyl, C$_{1-4}$ haloalkyl, C$_{1-6}$ alkoxy, C$_{1-4}$ haloalkoxy, —(CR$^4$R$^5$)$_c$S(O)$_b$R$^6$, S(O)$_b$R$^6$, —OSO$_2$R$^6$ and —N(R$^7$)SO$_2$R$^6$; or two groups R$^2$, on adjacent carbon atoms of the phenyl ring may, together with the carbon atoms to which they are attached, form a 5- or 6-membered saturated or unsaturated heterocyclic ring containing up to three ring heteroatoms selected from nitrogen, oxygen and sulphur, which ring may be optionally substituted by one or more groups selected from halogen, nitro, C$_{1-4}$ alkyl, C$_{1-4}$ alkoxy, C$_{1-4}$ haloalkyl, C$_{1-4}$ haloalkoxy and —S(O)$_b$R$^6$, it being understood that a sulphur atom, where present in the ring, may be in the form of a group —SO— or —SO$_2$—;
R$^3$ is C$_{1-4}$ alkyl;
R$^4$ and R$^5$ are independently hydrogen or C$_{1-4}$ alkyl;
R$^6$ is C$_{1-4}$ alkyl, or phenyl or benzyl, each of phenyl and benzyl optionally bearing from one or five substituents which may be the same of different selected from the group consisting of halogen, C$_{1-4}$ alkyl, C$_{1-4}$ alkoxy, C$_{1-4}$ haloalkyl, C$_{1-4}$ haloalkoxy, nitro and —S(O)$_b$CH$_3$;
R$^7$ is hydrogen or C$_{1-6}$ alkyl;
a is an integer from one to five;
b is zero, one or two; and
c is one or two (where c is two, the groups (CR$^4$R$^5$) may be the same or different.

Suitably R is hydrogen; R$^1$ is cyclopropyl; R$^2$ is halogen (preferably chloro), —S(O)$_b$CH$_3$, or C$_{1-4}$ haloalkyl (preferably trifluoromethyl); and a is two.

Particularly preferred compounds of formula (IA) include 5-cyclopropyl-4-(2-methylsulfonyl-4-trifluoromethyl)benzoylisoxazole (isoxaflutole) and 4-(2-chloro-4-methylsulphonyl)benzoyl-5-cyclopropylisoxazole (isoxachlortole).

Suitably, the triketone is a compound of formula (IB),

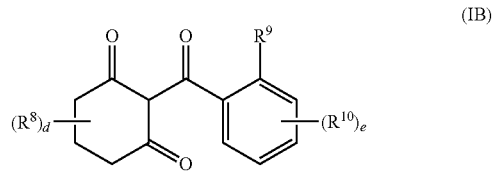

wherein each R$^8$ independently represents (C$_{1-4}$)allyl or —CO$_2$R$^{11}$;
R$^9$ represents a halogen atom; a straight- or branched-chain alkyl or alkoxy group containing up to six carbon atoms which is optionally substituted by one or more groups —$OR^{12}$ or one or more halogen atoms; or a group selected from nitro, cyano, —$CO_2R^{13}$, —$S(O)_fR^{12}$, —$O(CH_2)_gOR^{12}$, —$COR^{13}$, —$NR^{13}R^{14}$, —$SO_2NR^{13}R^{14}$, —$CONR^{13}R^{14}$, —$CSNR^{13}R^{14}$ and —$OSO_2R^{15}$;

each $R^{10}$ independently represents halo, nitro, cyano, $S(O)_f R^{16}$, $OS(O)_f R^{16}$, $C_{1-6}$ alkyl, $C_{1-6}$ alkoxy, $C_{1-6}$ haloalkyl, $C_{1-6}$ haloalkoxy, carboxy, $C_{1-6}$ alkylcarbonyloxy, $C_{1-6}$ alkoxycarbonyl, $C_{1-6}$ alkylcarbonyl, amino, $C_{1-6}$ alkylamino, $C_{1-6}$ dialkylamino having independently the stated number of carbon atoms in each alkyl group, $C_{1-6}$ alkylcarbonylamino, $C_{1-6}$ alkoxycarbonylamino, $C_{1-6}$ alkylaminocarbonylamino, $C_{1-6}$ dialkylaminocarbonylamino having independently the stated number of carbon atoms in each alkyl group, $C_{1-6}$ alkoxycarbonyloxy, $C_{1-6}$ alkylaminocarbonyloxy, $C_{1-6}$ dialkylcarbonyloxy, phenylcarbonyl, substituted phenylcarbonyl, phenylcarbonyloxy, substituted phenylcarbonyloxy, phenylcarbonylamino, substituted phenylcarbonylamino, phenoxy or substituted phenoxy;

$R^{11}$ is $C_{1-4}$ alkyl;

$R^{12}$ represents a straight- or branched-chain alkyl group containing up to six carbon atoms which is optionally substituted by one or more halogen atoms;

$R^{13}$ and $R^{14}$ each independently represents a hydrogen atom; or a straight- or branched-chain alkyl group containing up to six carbon atoms which is optionally substituted by one or more halogen atoms;

$R^{15}$ represents a straight- or branched-chain alkyl, alkenyl or alkynyl group containing up to six carbon atoms optionally substituted by one or more halogen atoms; or a cycloalkyl group containing from three to six carbon atoms;

$R^{16}$ represents a straight- or branched-chain alkyl group containing up to six carbon atoms which is optionally substituted by one or more halogen atoms;

d is zero or an integer from one to six;

e is zero or an integer from one to four;

f is zero, one or two; and g is one, two or three.

Suitably, $R^9$ is chloro, bromo, nitro, cyano, $C_{1-4}$ alkyl, —$CF_3$, —$S(O)_f R^{12}$, or —$OR^{12}$; each $R^{10}$ is independently chloro, bromo, nitro, cyano, $C_{1-4}$ alkyl, —$CF_3$, —$OR^{12}$, —$OS(O)_f R^{16}$ or —$S(O)_f R^{16}$; d is zero and e is one or two.

Preferred compounds of formula (IB) are 2-(2'-nitro-4'-methylsulphonylbenzoyl)-1,3-cyclohexanedione (mesotrione), 2-(2'-nitro-4'-methylsulphonyloxybenzoyl)-1,3-cyclohexanedione, 2-(2'-chloro-4'-methylsulphonylbenzoyl)-1,3-cyclohexanedione (sulcotrione), 4,4-dimethyl-2-(4-methanesulphonyl-2-nitrobenzoyl)-1,3-cyclohexanedione, 2-(2-chloro-3-ethoxymethanesulphonylbenzoyl)-5-methyl-1,3-cyclohexanedione and 2-(2-chloro-3-ethoxy-4-ethanesulphonylbenzoyl)-5-methyl-1,3-cyclohexanedione; most preferably is 2-(2'-nitro-4'-methylsulphonyl benzoyl)1,3-cyclohexanedione.

The compounds of formula (IB) may exist in enolic tautomeric forms that may give rise to geometric isomers. Furthermore, in certain cases, the various substituents may contribute to optical isomerism and/or stereoisomerism. All such tautomeric forms, racemic mixtures and isomers are included within the scope of the present invention.

Alternatively, the triketone is a compound of formula (IC)

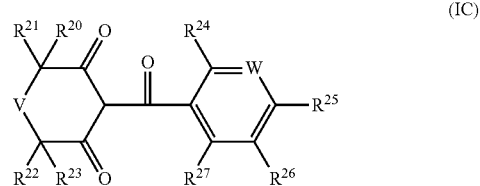

(IC)

wherein V is $C_{1-2}$ alkylene, which may be mono- or polysubstituted by $R^{29}$; or, when $R^{21}$ and $R^{22}$ are other than $C_{2-3}$ alkylene, W may additionally be carbonyl, oxygen or —$NR^{30}$—;

W is $CR^{31}$ or $N(O)_g$;

$R^{20}$, $R^{21}$, $R^{22}$ and $R^{23}$ are independently hydrogen, $C_{1-4}$ alkyl, phenyl, $C_{1-4}$ alkoxy, halogen, hydroxy, cyano, hydroxycarbonyl or $C_{1-4}$ alkoxycarbonyl; or $R^{21}$ and $R^{22}$ together are $C_{2-3}$ alkylene, which may be mono- or polysubstituted by $R^{28}$;

$R^{24}$ is hydrogen, $C_{1-6}$ alkyl, $C_{1-6}$ haloalkyl, $C_{2-6}$ alkenyl, $C_{2-6}$ haloalkenyl, $C_{1-2}$ alkoxycarbonyl- or phenyl-substituted vinyl, $C_{2-6}$ alkynyl, $C_{2-6}$ haloalkynyl, trimethylsilyl-, hydroxy-, $C_{1-6}$ alkoxy-, C alkoxycarbonyl- or phenyl-substituted ethynyl, $C_{3-6}$ allenyl, $C_{3-6}$ cycloalkyl, halo- or $C_{1-3}$ alkoxymethyl-substituted $C_{3-6}$ cycloalkyl, $C_{1-6}$ alkoxy, $C_{3-6}$ alkenyloxy, $C_{3-6}$ alkynyloxy, $C_{1-6}$ haloalkoxy, $C_{3-6}$ haloalkenyloxy, cyano-$C_{1-4}$ alkoxy, $C_{1-4}$ alkoxy-$C_{1-4}$ alkoxy, $C_{1-4}$ alkylthio-$C_{1-4}$ alkoxy, $C_{1-4}$ alkylsulfinyl-$C_{1-4}$ alkoxy, $C_{1-4}$ alkylsulfonyl-$C_{1-4}$ alkoxy, $C_{1-4}$ alkoxycarbonyl-$C_{1-4}$ alkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, $C_{1-4}$ alkoxycarbonyl-$C_{1-4}$ alkylthio, $C_{1-4}$ alkoxycarbonyl-$C_{1-4}$ alkylsulfinyl, $C_{1-4}$ alkoxycarbonyl-$C_{1-4}$ alkylsulfonyl, $C_{1-6}$ alkylamino, di($C_{1-6}$ alkyl)amino, $C_{1-3}$ alkoxy-$C_{1-3}$ alkylamino, $C_{1-3}$ alkoxy-$C_{1-3}$ alkyl-N($C_{1-3}$ alkyl), $C_{1-6}$ alkylaminosulfonyl, di($C_{1-6}$ alkyl)aminosulfonyl, $C_{1-4}$ alkylsulfonyloxy, $C_{1-4}$ haloalkylsulfonyloxy, $C_{1-4}$ alkylsulfonylamino, $C_{1-4}$ alkylsulfonyl-N($C_{1-4}$ alkyl), cyano, carbamoyl, $C_{1-4}$ alkoxycarbonyl, formyl, halogen, rhodano, amino, hydroxy-$C_{1-4}$ alkyl, $C_{1-4}$ alkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, cyano-$C_{1-4}$ alkyl, $C_{1-6}$ alkylcarbonyloxy-$C_{1-4}$ alkyl, $C_{1-4}$ alkoxycarbonyl-$C_{1-4}$ alkyl, $C_{1-4}$ alkoxycarbonyloxy-$C_{1-4}$ alkyl, rhodano-$C_{1-4}$ alkyl, phenyl-$C_{1-4}$ alkyl, phenoxy-$C_{1-4}$ alkyl, benzyloxy-$C_{1-4}$ alkyl, benzoyloxy-$C_{1-4}$ alkyl, (2-oxiranyl)-$C_{1-4}$ alkyl, $C_{1-4}$ alkylamino-$C_{1-4}$ alkyl, di($C_{1-4}$ alkyl)amino-$C_{1-4}$ alkyl, $C_{1-12}$ alkylthiocarbonyl-$C_{1-4}$ alkyl or formyl-$C_{1-4}$ alkyl, or benzylthio, benzylsulfinyl, benzylsulfonyl, benzyloxy, benzyl, phenyl, phenoxy, phenylthio, phenylsulfinyl or phenylsulfonyl, wherein the phenyl-containing groups may themselves be substituted by $C_{1-3}$ alkyl, $C_{1-3}$ haloalkyl, $C_{1-3}$ alkoxy, $C_{1-3}$ haloalkoxy, halogen, cyano or by nitro; or $R^{24}$ is a three- to ten-membered monocyclic or fused bicyclic ring system, which may be aromatic, saturated or partially saturated and may contain from 1 to 4 hetero atoms selected from nitrogen, oxygen and sulfur, wherein the ring system is bonded to the group W-containing aromatic ring by way of a $C_{1-4}$ alkylene, $C_{2-4}$ alkenylene or $C_{2-4}$ alkynylene bridge which may be interrupted by oxygen, —N($C_{1-4}$ alkyl)-, sulfur, sulfinyl, sulfonyl or by carbonyl, and each ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, $C_{1-6}$ haloalkoxy, $C_{3-6}$ alkenyloxy, $C_{3-6}$ alkynyloxy, hydroxy, mercapto, $C_{1-6}$ alkylthio, $C_{1-6}$ haloalkylthio, $C_{3-6}$ alkenylthio, $C_{3-6}$ haloalkenylthio, $C_{3-6}$ alkynylthio, $C_{1-4}$ alkoxy-$C_{1-3}$ alkylthio, $C_{1-4}$ alkylcarbonyl-$C_{1-3}$ alkylthio, $C_{1-4}$ alkoxycarbonyl-$C_{1-3}$ alkylthio, cyano-$C_{1-3}$-alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-4}$ alkylaminosulfonyl, di($C_{1-4}$ alkyl)aminosulfonyl, di($C_{1-4}$ alkyl)amino, halogen, cyano, nitro, phenyl and/or by benzylthio, wherein phenyl and benzylthio may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein substituents on the nitrogen in the heterocyclic ring are other than halogen; or $R^{24}$ is the group —$D_1$—$D_3$ or the group —$D_2$—$D_1$—$D_3$;

$R^{25}$ is hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, $C_{1-6}$ alkylsulfonyloxy, hydroxy, mercapto, amino, $C_{1-6}$ alkylamino, di($C_{1-6}$ alkyl)amino, $C_{1-4}$ alkylsulfonylamino, $C_{1-4}$ alkylsulfonyl-N($C_{1-4}$ alkyl)-, $C_{1-6}$ alkylaminosulfonyl, di($C_{1-4}$ alkyl)aminosulfonyl, cyano, halogen, $C_{1-4}$ alkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, triazolyl, phenyl, phenylthio, phenylsulfinyl, phenylsulfonyl or phenoxy, wherein the phenyl-containing groups may be substituted by $C_{1-3}$ alkyl, $C_{1-3}$ haloalkyl, $C_{1-3}$ alkoxy, $C_{1-3}$ haloalkoxy, halogen, cyano or by nitro;

$R^{26}$ is hydrogen, $C_{1-6}$ alkyl, hydroxy, $C_{1-6}$ alkoxy, $C_{1-6}$ haloalkoxy, $C_{3-6}$ alkenyloxy, $C_{3-6}$ haloalkenyloxy, $C_{3-6}$ alkynyloxy, $C_{1-4}$ alkylcarbonyloxy, $C_{1-4}$ alkylsulfonyloxy, phenylsulfonyloxy, $C_{1-4}$ alkylthio, $C_{1-4}$ alkylsulfinyl, $C_{1-4}$ alkylsulfonyl, $C_{1-4}$ alkylamino, di($C_{1-4}$ alkyl)amino, $C_{1-4}$ alkoxycarbonyl, $C_{1-4}$ haloalkyl, formyl, cyano, halogen, phenyl or phenoxy, wherein the phenyl-containing groups may themselves be substituted by $C_{1-3}$ alkyl, $C_{1-3}$ haloalkyl, $C_{1-3}$ alkoxy, $C_{1-3}$ haloalkoxy, halogen, cyano or by nitro; or $R^{26}$ is a three- to ten-membered monocyclic or, together with $R^{25}$ or $R^{27}$, fused bicyclic ring system, which may contain from 1 to 4 hetero atoms selected from nitrogen, oxygen and sulfur, wherein, when the ring system is not fused, it is bonded to the W-containing aromatic ring, either directly or by way of a $C_{1-4}$ alkylene, $C_{2-4}$ alkenylene or $C_{2-4}$ alkynylene bridge which may be interrupted by oxygen, —N($C_{1-4}$ alkyl)-, sulfur, sulfinyl, sulfonyl or by carbonyl, and the ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, $C_{1-6}$ haloalkoxy, $C_{3-6}$ alkenyloxy, $C_{3-6}$ alkynyloxy, $C_{1-6}$ alkylthio, $C_{1-6}$ haloalkylthio, $C_{3-6}$ alkenylthio, $C_{3-6}$ haloalkenylthio, $C_{3-6}$ alkynylthio, $C_{1-4}$ alkoxy-$C_{1-2}$ alkylthio, $C_{1-4}$ alkylcarbonyl-$C_{1-2}$ alkylthio, $C_{1-4}$ alkoxycarbonyl-$C_{1-2}$ alkylthio, cyano-$C_{1-4}$ alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-4}$ alkylaminosulfonyl, di($C_{1-4}$ alkyl)aminosulfonyl, amino, $C_{1-4}$ alkyl amino, di($C_{1-4}$ alkyl)amino, halogen, cyano, nitro, phenyl and by/or benzylthio, wherein phenyl and benzylthio may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein substituents on the nitrogen in the heterocyclic ring are other than halogen;

$R^{27}$ is hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, amino, $C_{1-6}$ alkylamino, di($C_{1-6}$ alkyl)amino, $C_{1-4}$ alkylsulfonyl-N($C_{1-4}$ alkyl)-, $C_{1-6}$ alkylaminosulfonyl, di($C_{1-6}$ alkyl)aminosulfonyl, cyano, halogen, $C_{1-4}$ alkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, phenyl, phenylthio, phenylsulfinyl, phenylsulfonyl or phenoxy, wherein phenyl groups may themselves be substituted by $C_{1-3}$ alkyl, $C_{1-3}$ haloalkyl, $C_{1-3}$ alkoxy, $C_{1-3}$ haloalkoxy, halogen, cyano or by nitro;

$R^{28}$ and $R^{29}$ are each independently hydrogen, $C_{1-4}$ alkyl, phenyl, $C_{1-4}$ alkoxy, halogen, hydroxy, cyano, hydroxycarbonyl or $C_{1-4}$ alkoxycarbonyl;

$R^{30}$ is $C_{1-4}$ alkyl, alkoxycarbonyl or $C_{1-4}$ alkylcarbonyl;

$R^{31}$ is hydrogen, $C_{1-6}$ alkyl, hydroxy, $C_{1-6}$ alkoxy, $C_{1-6}$ haloalkoxy, $C_{3-6}$ alkenyloxy, $C_{3-6}$ haloalkenyloxy, $C_{3-6}$ alkynyloxy, $C_{1-4}$ alkylcarbonyloxy, $C_{1-4}$ alkylsulfonyloxy, phenylsulfonyloxy, $C_{1-6}$ alkylthio, $C_{1-6}$ alkylsulfinyl, $C_{1-6}$ alkylsulfonyl, $C_{1-6}$ alkylamino, di($C_{1-6}$ alkyl)amino, $C_{1-3}$ alkoxy-$C_{1-3}$ alkylamino, $C_{1-3}$ alkoxy-$C_{1-3}$ alkyl-N($C_{1-3}$ alkyl)-, $C_{1-4}$ alkoxycarbonyl, $C_{1-6}$ haloalkyl, formyl, cyano, halogen, phenyl or phenoxy, wherein the phenyl-containing groups may themselves be substituted by $C_{1-3}$ alkyl, $C_{1-3}$ haloalkyl, $C_{1-3}$ alkoxy, $C_{1-3}$ haloalkoxy, halogen, cyano or by nitro;

or $R^{31}$ is a three- to ten-membered monocyclic or, together with $R^{24}$ or $R^{25}$ fused bicyclic ring system, which may be interrupted once or up to three times by heterocyclic substituents selected from oxygen, sulfur, S(O), $SO_2$, N($R^{32}$), carbonyl and C(=$NOR^{33}$), and wherein, when the ring system is not fused, it is bonded to the carbon atom of the substituent W, either directly or by way of a $C_{1-4}$ alkylene, $C_{2-4}$ alkenylene or $C_{2-4}$ alkynylene bridge which may be interrupted by oxygen, —N($C_{1-4}$ alkyl)-, sulfur, sulfinyl or by sulfonyl, and the ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, $C_{1-6}$ haloalkoxy, $C_{3-6}$ alkenyloxy, $C_{3-6}$ alkynyloxy, $C_{1-6}$ alkylthio, $C_{1-6}$ haloalkylthio, $C_{3-6}$ alkenylthio, $C_{3-6}$ haloalkenylthio, $C_{3-6}$ alkynylthio, $C_{1-4}$ alkoxy-$C_{1-2}$ alkylthio, $C_{1-4}$ alkylcarbonyl-$C_{1-2}$-alkylthio, $C_{1-4}$ alkoxycarbonyl-$C_{1-2}$ alkylthio, cyano-$C_{1-4}$ alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-4}$ alkylaminosulfonyl, di($C_{1-4}$ alkyl)aminosulfonyl, di($C_{1-4}$ alkyl)amino, halogen, cyano, nitro, phenyl, benzyloxy and/or by benzylthio, and wherein the phenyl-containing groups may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein substituents on the nitrogen in the heterocyclic ring are other than halogen;

or $R^{31}$ is the group —$D_4$—$D_6$ or the group —$D_5$—$D_4$—$D_6$;

$R^{32}$ is hydrogen, $C_{1-4}$ alkyl, $C_{1-4}$ alkylthio-$C_{1-4}$ alkylcarbonyl, $C_{1-4}$ alkylsulfinyl-$C_{1-4}$-alkylcarbonyl, $C_{1-4}$ alkylsulfonyl-$C_{1-4}$ alkylcarbonyl, $C_{1-4}$ alkoxycarbonyl, $C_{1-4}$ alkylcarbonyl, phenylcarbonyl or phenyl, wherein the phenyl groups may be substituted by $C_{1-4}$ alkyl, $C_{1-4}$ haloalkyl, $C_{1-4}$ alkoxy, $C_{1-4}$ haloalkoxy, $C_{1-4}$ alkylcarbonyl, $C_{1-4}$ alkoxycarbonyl, $C_{1-4}$ alkylamino, di($C_{1-4}$ alkyl)amino, $C_{1-4}$ alkylthio, $C_{1-4}$ alkylsulfinyl, $C_{1-4}$ alkyl-$SO_2$, $C_{1-4}$ alkyl-$S(O)_2O$, $C_{1-4}$ haloalkylthio, $C_{1-4}$ haloalkylsulfinyl, $C_{1-4}$ haloalkyl-$SO_2$, $C_{1-4}$ haloalkyl-$S(O)_2O$, $C_{1-4}$ alkyl-$S(O)_2NH$, $C_{1-4}$ alkyl-$S(O)_2N(C_{1-4}$alkyl)-, halogen, nitro or by cyano;

$R^{33}$ is hydrogen, $C_{1-4}$ alkyl, $C_{3-4}$ alkenyl, $C_{3-4}$ alkynyl or benzyl;

h is 0 or 1;

$D_1$ is oxygen, —O(CO)—, —(CO)O—, —O(CO)O—, —N($C_{1-4}$ alkyl)—O—, —O—N($C_{1-4}$ alkyl)-, thio, sulfinyl, sulfonyl, —SO$_2$N($C_{1-4}$alkyl)-, —N($C_{1-4}$ alkyl)SO$_2$—, —N($C_{1-2}$ alkoxy-$C_{1-2}$ alkyl)SO$_2$— or —N($C_{1-4}$ alkyl)-;

$D_2$ is a $C_{1-6}$ alkylene, $C_{3-6}$ alkenylene or $C_{3-6}$ alkynylene chain, which may be mono- or poly-substituted by halogen or by $D_7$, the unsaturated bonds of the chain not being bonded directly to the substituent $D_1$;

$D_3$ and $D_6$ are each independently of the other a $C_{1-8}$ alkyl, $C_{3-6}$ alkenyl or $C_{3-6}$ alkynyl group, which may be mono- or poly-substituted by halogen, hydroxy, amino, formyl, nitro, cyano, mercapto, carbamoyl, $C_{1-6}$ alkoxy, $C_{1-6}$ alkoxycarbonyl, $C_{2-6}$ alkenyl, $C_{2-6}$ haloalkenyl, $C_{2-6}$ alkynyl, $C_{2-6}$ haloalkynyl, $C_{3-6}$ cycloalkyl, halo-substituted $C_{3-6}$ cycloalkyl, $C_{3-6}$ alkenyloxy, $C_{3-6}$ alkynyloxy, $C_{1-6}$haloalkoxy, $C_{3-6}$ haloalkenyloxy, cyano-$C_{1-6}$ alkoxy, $C_{1-6}$ alkoxy-$C_{1-6}$ alkoxy, $C_{1-6}$ alkoxy-$C_{1-6}$ alkoxy-$C_{1-6}$ alkoxy, $C_{1-6}$ alkylthio-$C_{1-6}$ alkoxy, $C_{1-6}$ alkylsulfinyl-$C_{1-6}$ alkoxy, $C_{1-6}$ alkylsulfonyl-$C_{1-6}$ alkoxy, $C_{1-6}$ alkoxycarbonyl-$C_{1-6}$ alkoxy, $C_{1-6}$ alkoxycarbonyl, $C_{1-6}$ alkylcarbonyl, $C_{1-6}$ alkylthio, $C_{1-4}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, oxiranyl which may itself be substituted by $C_{1-6}$ alkyl, (3-oxetanyl)-oxy which may itself be substituted by $C_{1-6}$ alkyl, benzyloxy, benzylthio, benzylsulfinyl, benzylsulfonyl, $C_{1-6}$ alkylamino, di($C_{1-6}$ alkyl)amino, $C_{1-4}$ alkyl-S(O)$_2$O, di($C_{1-4}$ alkyl)aminosulfonyl, rhodano, phenyl, phenoxy, phenylthio, phenylsulfinyl or by phenylsulfonyl, and wherein the phenyl- or benzyl-containing groups may themselves be substituted by one or more $C_{1-6}$ alkyl, $C_{1-6}$ haloalkyl, $C_{1-6}$ alkoxy, $C_{1-6}$ haloalkoxy, halogen, cyano, hydroxy or nitro groups; or $D_3$ and $D_6$ are each independently of the other phenyl, which may be mono- or poly-substituted by $C_{1-6}$ alkyl, $C_{1-6}$ haloalkyl, $C_{1-6}$ alkoxy, $C_{1-6}$ haloalkoxy, halogen, cyano, hydroxy or by nitro; or $D_3$ and $D_6$ are each independently of the other $C_{3-6}$ cycloalkyl, $C_{1-6}$ alkoxy- or $C_{1-6}$ alkyl-substituted $C_{3-6}$ cycloalkyl, 3-oxetanyl or $C_{1-6}$ alkyl-substituted 3-oxetanyl; or $D_3$ and $D_6$ are each independently of the other a three- to ten-membered monocyclic or fused bicyclic ring system, which may be aromatic, saturated or partially saturated and may contain from 1 to 4 hetero atoms selected from nitrogen, oxygen and sulfur, wherein the ring system is bonded to the substituent $D_1$ or $D_4$ directly or by way of a $C_{1-4}$ alkylene, $C_{2-4}$ alkenylene, $C_{2-4}$ alkynylene, —N($C_{1-4}$ alkyl)—$C_{1-4}$ alkylene, —S(O)—$C_{1-4}$ alkylene or —SO$_2$—$C_{1-4}$ alkylene group, and each ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, hydroxy, $C_{1-6}$-haloalkoxy, $C_{3-6}$ alkenyloxy, $C_{3-6}$ alkynyloxy, mercapto, $C_{1-6}$ alkylthio, $C_{1-6}$ haloalkylthio, $C_{3-6}$ alkenylthio, $C_{3-6}$ haloalkenylthio, $C_{3-6}$ alkynylthio, $C_{1-3}$ alkoxy-$C_{1-3}$ alkylthio, $C_{1-4}$ alkylcarbonyl-$C_{1-2}$ alkylthio, $C_{1-4}$ alkoxycarbonyl-$C_{1-2}$ alkylthio, cyano-$C_{1-3}$ alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-2}$alkylaminosulfonyl, di($C_{1-2}$ alkyl)aminosulfonyl, di($C_{1-4}$ alkyl)amino, $C_{1-6}$ carbonylamino, halogen, cyano, nitro, phenyl, benzyloxy and/or by benzylthio, wherein the phenyl groups may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein the substituents on the nitrogen in the heterocyclic ring are other than halogen;

$D_4$ is oxygen, —O(CO)—, —(CO)O—, —O(CO)O—, —N($C_{1-4}$ alkyl)-O—, —O—N($C_{1-4}$ alkyl)-, sulfur, sulfinyl, sulfonyl, —SO$_2$N($C_{1-4}$ alkyl)-, —N($C_{1-4}$ alkyl)SO$_2$—, —N($C_{1-2}$ alkoxy-$C_{1-2}$ alkyl)SO$_2$— or —N($C_{1-4}$ alkyl)-;

$D_5$ is a $C_{1-6}$ alkylene, $C_{3-6}$ alkenylene or $C_{3-6}$ alkynylene chain, which may be mono- or poly-substituted by halogen or by $D_8$, the unsaturated bonds of the chain not being bonded directly to the substituent $D_4$;

$D_7$ and $D_8$ are each independently of the other hydroxy, $C_{1-6}$ alkoxy, ($C_{3-6}$ cycloalkyl)oxy, $C_{1-6}$ alkoxy-$C_{1-6}$ alkoxy, $C_{1-6}$ alkoxy-$C_{1-6}$ alkoxy-$C_{1-6}$ alkoxy or $C_{1-6}$ alkylsulfonyloxy;

and agronomically acceptable salts/N-oxides/isomers/enantiomers of such compounds.

Alternatively, the triketone may be present in an enolic form and is a compound of formula (ID)

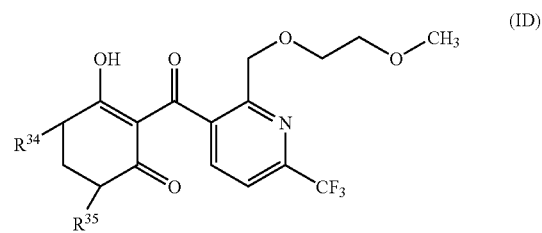

wherein $R^{34}$ and $R^{35}$ are both hydrogen or together form an ethylene bridge.

The compound of formula (ID) wherein both $R^{34}$ and $R^{35}$ are hydrogen is hereinafter referred to as compound (IDa), and the compound of formula (I) wherein $R^{34}$ and $R^{35}$ together form an ethylene bridge is hereinafter referred to as compound (IDb).

Suitably, the pyrazole is a compound of formula (IE)

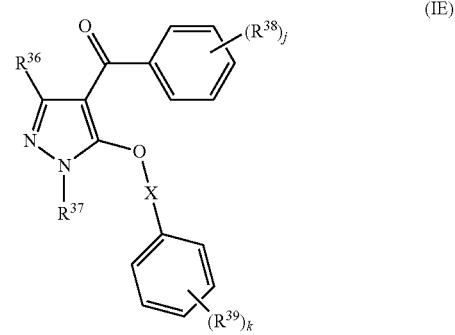

wherein $R^{36}$, $R^{37}$, $R^{38}$ and $R^{39}$ are each independently selected from hydrogen, halo or $C_{1-4}$ alkyl;

X is —SO$_2$— or —CH$_2$CO—;

j is 2 or 3; and k is zero or 1.

Suitably $R^{36}$, $R^{37}$, $R^{38}$ and $R^{39}$ are each independently hydrogen, chloro or methyl.

Preferred compounds of formula (IE) include 2-[[4-(2,4-dichloro-3-methylbenzoyl)-1,3-dimethyl-1H-pyrazol-5-yl]oxy]-1-(4-methylphenyl)ethanone (benzofenap), (2,4-dichlorophenyl)[1,3-dimethyl-5-[[(4-methylphenyl)sulfonyl]oxy]-1H-pyrazol-4-yl]methanone (pyrazolynate) and 2-[[4-(2,4-dichlorobenzoyl)-1,3-dimethyl-1H-pyrazol-5-yl]oxy]-1-phenylethanone (pyrazoxyfen).

Benzobicyclon is a compound of formula (IF)

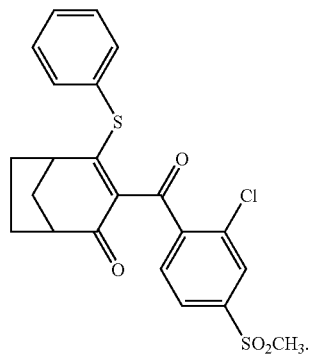

Ketospiradox is a compound of formula (IG)

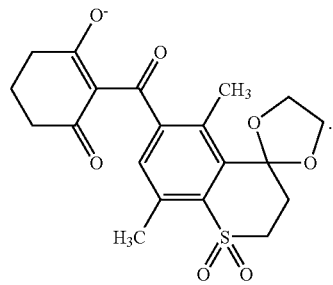

Agriculturally acceptable salts for use in the present invention include salts the cations or anions of which are known and accepted in the art for the formation of salts for agricultural or horticultural use. Useful salts for practice of the invention may be formed from compounds of formulae (IA) to (IG) using amines, alkali metal bases, alkaline earth metal bases, quaternary ammonium bases, and metal chelates. Also included are metal chelates of compounds of formulae (IA) to (IG), particularly compounds of formula (IB), including salts of di- and trivalent transition metal ions such as $Cu^{+2}$, $Zn^{+2}$, $Co^{+2}$, $Ni^{+2}$, $Ca^{+2}$, $Al^{+3}$, $Ti^{+3}$, $Fe^{+3}$, $Fe^{+3}$, $Ba^{+2}$, $Cs^{+2}$, and also $[CH_3(CH_2)_7]3N$.

Examples of suitable amines for ammonium salt formation that come into consideration are ammonia as well as primary, secondary and tertiary $C_{1-18}$ alkylamines, $C_{1-4}$ hydroxyalkylamines and $C_{2-4}$ alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary aryl amines for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

The selection of a particular metal ion to form a metal chelate compound of a compound of formulae (IA) to (IG); particularly (IB), will depend upon the dione compound to be chelated. For example, metal chelates of compounds of formula (IB) and their preparation are described, inter alia, in PCT Publication No. WO97/27748. Metal chelates of compounds of formula (IB) have the general structure:

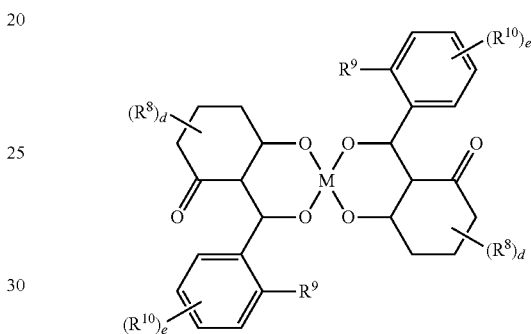

wherein $R^8$, $R^9$, $R^{10}$, d and e are as hereinbefore defined, and wherein M represents a di- or trivalent metal ion such as $Cu^{+2}$, $Zn^{+2}$, $Co^{+2}$, $Ni^{+2}$, $Ca^{+2}$, $Al^{+3}$, $Ti^{+3}$, $Fe^{+2}$, $Fe^{+3}$, $Ba^{+2}$, $Cs^{+2}$ and also $[CH_3(CH_2)_7]_3N$. The preferred metal ions are divalent transition metal ions, particularly $Cu^{+2}$, $Co^{+2}$, $Ni^{+2}$, and $Zn^{+2}$; with $Cu^{+2}$ being especially preferred. Any appropriate salt which would be a source of a di- or trivalent metal ion may be used to form the metal chelate of the dione compound in accordance with this invention. Particularly suitable salts include: chlorides, sulphates, nitrates, carbonates, phosphates and acetates.

Insecticides suitable for use in the present invention include Abamectin, Acephate, Acetamiprid, Acrinathrin, Acrylonitrile, Alanycarb, Aldicarb, Aldoxycarb, Aldrin, Allethrin (1R-isomers), Allyxycarb, Alpha-cypermethrin, Phosphine (Aluminium Phosphide), Amidithion, Aminocarb, Amiton, Amitraz, Anabasine, Athidathion, Azadirachtin, Azamethiphos, Azinphos-ethyl, Azinphos-methyl, Azothoate, *Bacillus sphaericus, Bacillus thuringiensis, Bacillus thuringiensis* delta endotoxins, Barium polysulfide, Bendiocarb, Benfuracarb, Bensultap, Benzoximate, Beta-cyfluthrin, Beta-cypermethrin, Bifenthrin, Bioallethrin, Bioallethrin S-cyclopentenyl isomer, Biopemiethrin, Bioresmethrin, Bistrifluron, Borax, Bromfenvinfos, Bromophos, Bromophos-ethyl, Bufencarb, Buprofezin, Butacarb, Butathiofos, Butocarboxim, Butonate, Butoxycarboxim, Cadusafos, Hydrogen cyanide, Calcium polysulfide, Camphechlor, Carbanolate, Carbaryl, Carbofuran, Carbon disulfide, Carbon tetrachloride, Carbophenothion, Carbosulfan, Cartap, Chlorbicyclen, Chlordane, Chlordecone, Chlordimeform, Chlorethoxyfos, Chlorfenapyr, Chlorfenvinphos, Chlorfluazuron, Chlormephos, Chloropicrin, Chlorphoxim, Chlorprazophos, Chlorpyrifos, Chlorpyrifos-methyl, Chlorthiophos, Chromafenozide, Clothianidin, Coumaphos, Coumithoate, Crotoxyphos, Crufomate, Cryolite, Cyanofenphos, Cyanophos, Cyanthoate, Cycloprothrin, Cyfluthrin, Cyhalothrin, Cypermethrin, Alpha-cypermethrin, Beta-Cypermethrin, Theta-cypermethrin, Zeta-cypermethrin, Cyphenothrin, Cyromazine, Dazomet, Bromo-DDT, DDT, pp'-DDT, Decarbofuran, Deltamethrin, Demephion, Demephion-O, Demephion-S, Demeton, Demeton-O, Demeton-S, Demeton-methyl, Demeton-O-methyl, Demeton-S-methyl, Demeton-S-methylsulphon, Diafenthiuron, Dialifos, Diazinon, Dicapthon, Dichlofenthion, Dichlorvos, Dicrotophos, Dicyclanil, Dieldrin, Diflubenzuron, Dimefox, Dimethoate, Dimethrin, Dimethylvinphos, Dimetilan, Dinex, Dinotefuran, Diofenolan, Dioxabenzofos, Dioxacarb, Dioxathion, Disulfoton, Dithicrofos, DNOC, Emamectin, EMPC, Empenthrin, Endosulfan, Endothion, EPN, Epofenonane, Esfenvalerate, Ethiofencarb, Ethion, Ethoate-methyl, Ethoprophos, Ethylene dibromide, Ethylene dichloride, Etofenprox, Etrimfos, Famphur, Fenchlorphos, Fenethacarb, Fenfluthrin, Fenitrothion, Fenobucarb, Fenoxycarb, Fenpirithrin, Fenpropathrin, Fensulfothion, Fenthion, Fenvalerate, Fipronil, Flonicamid, Flucofuron, Flucycloxuron, Flucythrinate, Flucythrinate, Flucythrinate, Flufenprox, Flumethrin, Fluvalinate, Fonofos, Formetanate, Formothion, Fosmethilan, Fospirate, Fosthiazate, Fosthietan, Furathiocarb, Furethrin, gamma-HCH, GY-81, Halofenozide, Heptachlor, Heptenophos, Hexaflumuron, Hydramethylnon, Hydrogen cyanide, Hydroprene, Imidacloprid, Imiprothrin, Indoxacarb, IPSP, Isazofos, Isobenzan, Isodrin, Isofenphos, Isoprocarb, Isopropyl O-(methoxyaminothiophosphoryl)salicylat, Isothioate, Isoxathion, Jodfenphos, Kelevan, Kinoprene, Lambda-cyhalothrin, Lirimfos, Lufenuron, Lythidathion, Phosphine, Malathion, Mazidox, Mecarbam, Mecarphon, Menazon, Mephosfolan, Mercurous chloride, Mesulfenfos, Metam, Methacrifos, Methamidophos, Methidathion, Methiocarb, Methocrotophos, Methomyl, Methoprene, Methothrin, Methoxychlor, Methoxyfenozide, Methyl bromide, Methyl isothiocyanate, Metolcarb, Metoxadiazone, Mevinphos, Mexacarbate, Milbemectin, Mipafox, Mirex, Monocrotophos, Morphothion, Naled, Nicotine, Nifluridide, Nitenpyram, Nithiazine, Nitrilacarb, Novaluron, Ölsäure, Omethoate, Oxamyl, Oxydemeton-methyl, Oxydeprofos, Oxydisulfoton, Parathion, Parathion-methyl, Pentachlorophenol, Permethrin, Petroleum Öl, Phenkapton, Phenothrin, Phenthoate, Phorate, Phosalone, Phosfolan, Phosmet, Phosnichlor, Phosphamidon, Phoxim, Phoxim-methyl, Pirimetaphos, Pirimicarb, Pirimiphos-ethyl, Pirimiphos-methyl, Prallethirin, Primidophos, Profenofos, Promacyl, Promecarb, Propaphos, Propetamphos, Propoxur, Prothiofos, Prothoate, Pymetrozine, Pyraclofos, Pyrazophos, Pyresmethrin, Pyrethrins, Pyridaben, Pyridaphenthion, Pyrimidifen, Pyrimitate, Pyriproxyfen, Quinalphos, Quinalphos-methyl, Quinothion, Resmethrin, Rotenone, RU 15525, Sabadilla, Schradan, Silafluofen, Sodium fluoride, Sodium hexafluorosilicate, Pentachlorophenol, Sophamide, Spinosad, Sulcofuron, Sulfluramid, Sulfotep, Sulfuryl fluoride, Sulprofos, Tau-fluvalinate, Tazimcarb, TDE, Tebufenozide, Tebupirimfos, Teflubenzuron, Tefluthrin, Temephos, TEPP, Terallethrin, Terbufos, Tetrachlorvinphos, Tetramethrin, Tetramethrin [(1R)-isomers], Thiacloprid, Thiamethoxam, Thicrofos, Thiocarboxime, Thiocyclam, Thiodicarb, Thiofanox, Thiometon, Thiosultap-sodium, Tolfenpyrad, Tralomethrin, Transfluthrin, Transpermethrin, Triazamate, Triazofos, Trichlorfon, Trichloronat, Tridec-4-enyl acetate, Trifenofos, Triflumuron, Trimethacarb, Triprene, Vamidothion, XMC, Xylylcarb, Spirodiclofen, Acetoprole, Fluacrypyrim, Pyridalyl, Noviflumuron, Flufenerim, Amidoflumet, Ethiprole, Acequinocyl, Etoxazole, Bifenazate, Spiromesifen and ZXI 8901. The above insecticides are described in the Pesticide Manual, 12$^{th}$ ed., British Crop Protection Council 2000.

In a preferred embodiment of the invention, the insecticide is not lambda-cyhalothrin when the HPPD-inhibiting herbicide is 2-(2'-nitro-4'-methylsulphonylbenzoyl)-1,3-cyclohexanedione (mesotrione).

Particularly preferred combinations of HPPD-inhibiting herbicide salt and insecticide include agrochemically acceptable salts of isoxaflutole, isoxachlortole, mesotrione, sulcotrione, Compound (IDa), Compound (IDb), benzofenap, pyrazolynate, pyrazoxyfen, Benzobicyclon or Ketospiradox with chlorpyrifos, chlorpyrifos-methyl, terbufos, tefluthrin or thiamethoxam.

In a further preferred embodiment of the invention, if the insecticide is terbufos or chlorpyrifos and the HPPD-inhibiting herbicide is 2-(2'-nitro-4'-methylsulphonylbenzoyl)-1,3-cyclohexanedione (mesotrione), the herbicide is suitably given post-emergence.

The pesticidally active combination according to the invention can be used against a large number of agronomically important weeds, such as *Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica*. The combination according to the invention is suitable for all methods of application conventionally used in agriculture, e.g. pre-emergence application, post-emergence application and seed dressing. Suitably, at least the HPPD-inhibiting herbicide is applied post-emergence, in particular when applied with a organophosphate or carbamate insecticide. The combination according to the invention is suitable especially for controlling weeds in crops of useful plants, such as cereals, rape, sugar beet, sugar cane, plantation crops, rice, maize and soybeans, and also for non-selective weed control. "Crops" are to be understood also to include those crops which have been made tolerant to herbicides or classes of herbicides as a result of conventional methods of breeding or genetic engineering. The components used in the combination of the invention can be applied in a variety of ways known to those skilled in the art, at various concentrations. The rate at which the herbicidal components are applied will depend upon the particular type of weed to be controlled, the degree of control required, and the timing and method of application. In general, the components can be applied at an application rate of between about 10 g a.i./hectare (g/ha) and about 7500 g a.i./ha, based on the total amount of active ingredient. An application rate of between about 50 g a.i/ha and 5000 g a.i./ha is preferred. Suitably, the HPPD-inhibiting herbicide salt is applied at a rate of 1-500 g a.i./ha, preferably 50-250 g a.i/ha; and the insecticide compound is applied at a rate of 5-2500 g a.i/ha, preferably 50-2000 g a.i./ha. In an especially preferred embodiment of this invention, the components are administered in relative amounts sufficient to provide an application rate of at least 2000 g a.i./ha, of which the HPPD-inhibiting herbicide salt provides at least 100 g/ha. Generally the mixing ratios (by weight) of HPPD and Insecticide compound are from 1:2000 to 2000:1; preferably 1:200 to 200:1.

The components used in the combination of the invention may be administered simultaneously or sequentially. If administered sequentially, the components may be administered in any order in a suitable timescale, for example the insecticide may be administered at planting and the HPPD-inhibiting herbicide salt administered post-emergent.

If the components are administered simultaneously, they may be administered separately or as a tank mix or as a pre-formulated mixture of all the components or as a pre-formulated mixture of some of the components tank mixed with the remaining components.

Therefore, a yet further aspect of the invention provides a pesticidally active pre-mix composition comprising a HPPD-inhibiting herbicide in the form of an agrochemically acceptable salt and an insecticide, provided that the HPPD-inhibiting herbicide is not a compound of formula (A)

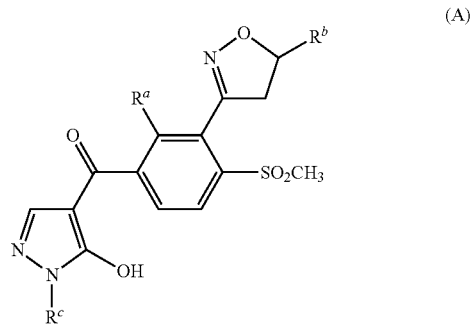

wherein $R^a$ is $C_{1-2}$ alkyl or chloro; $R^b$ is hydrogen or $C_{1-4}$ alkyl; and $R^c$ is $C_{1-4}$ alkyl.

A yet further aspect of the invention provides a pesticidally active combination or pre-mix composition comprising an HPPD inhibiting herbicide in the form of a salt and an insecticide as hereinbefore defined, in combination with one or more additional active ingredients. Such additional active ingredients may be other herbicides, fungicides, insecticides, or the like or safeners. In particular, the one or more additional active ingredients are herbicides and/or safeners. Examples of suitable additional herbicides and/or safeners for use in the present invention include atrazine, terbuthylazine, metolachlor, s-metolachlor, benoxacor, furilazole, dichlormid, flurazole acetochlor, p-dimethenamid, glyphosate, cloquintocet, fluxofenim, nicosulfuron, rimsulfuron, foramsulfuron, isoxadifene, prosulfuron, primisulfuron, dicamba, trifloxysulfuron and the like. The pesticidal combination may contain, in addition to the main two components, an additional one, two, three, four or more components of the additional herbicides and/or safeners listed above.

The present invention is also directed to methods of controlling undesired plant growth in crops of useful plants, said method comprising the application of a pesticidally active amount of the combination or pre-mix composition of the invention to the cultivated plant or its locus. The method is especially useful where the cultivated plant is maize or a cereal.

The present invention will now be further described with reference to the following examples.

EXAMPLE 1

Field tests were conducted in the following way: Corn was seeded with standard sowing implements and grown under natural conditions until the 2-3 leaf stage of corn was reached. Corn with or without insecticide treatments applied at seeding was grown at the same time. At 2-3 leaf stage, the herbicides only or in combination with the insecticide, if the insecticide has not been applied at seeding, was applied broadcast foliar over the top. At highest phytotoxicity levels for corn at five days after application and at maximal weed control levels at 16 days after application, the trial was evaluated. The results are shown in the following Table I:

TABLE I

| | | | | | Crop/Variety | | |
| | | | | | Corn 'NK58D1 | Sweet Corn 'Jubilee SS | Weed/ *Amaranthus retroflexus* |
| | | | | | | Rating Data Type | |
| | | | | | Phytotox. | Phytotox. | Weed Control |
| | | | | | | Rating Unit Scale | |
| | | All post applications with: | | | % | % | % |
| | | | | | Evaluation @ Days after last application | | |
| | | COC @ 1% V/V + | | | 5 | 5 | 16 |
| | Appln. | UAN @ 2.5% V/V | | Rate | | Scale Min-Max | |
| Trt | Timing | Treatment/Product | a.i. rate | Unit | 0-100 | 0-100 | 0-100 |
| 1 | | Check untreated | | | 0 | 0 | 0 |
| 2 | Post | Mesotrione | 105 | GA/Ha | 3.8 | 16.3 | 90 |
| 3 | Post | Mesotrione-Cu + s-metolachlor + benoxacor | 105(a.e) + 1053 + 52.5 | GA/Ha | 0 | 0 | 71.3 |
| 4 | Post | Mesotrione-Cu + s-metolachlor + atrazine + benoxacor | 105(a.e) + 1053 + 394 + 52.5 | GA/Ha | 2 | 1.3 | 95 |
| 5 | Post | Mesotrione-Cu | 105(a.e.) | GA/Ha | 0 | 0 | 87.5 |
| 6 | Post | Mesotrione | 210 | GA/Ha | 8.8 | 15 | 95 |
| 7 | Post | Mesotrione-Cu + s-metolachlor + benoxacor | 210(a.e) + 2105 + 105 | GA/Ha | 0 | 0 | 88.8 |
| 8 | Post | Mesotrione-Cu + s-metolachlor + atrazine + benoxacor | 210(a.e) + 2100 + 788 + 105 | GA/Ha | 6.3 | 1.3 | 95 |

TABLE I-continued

| | | | | Crop/Variety | | |
| | | | | Corn 'NK58D1' | Sweet Corn 'Jubilee SS' | Weed/ *Amaranthus retroflexus* |
| | | | | Rating Data Type | | |
| | | | | Phytotox. | Phytotox. | Weed Control |
| | | | | Rating Unit Scale | | |
| | | All post applications with: | | % | % | % |
| | | | | Evaluation @ Days after last application | | |
| | | COC @ 1% V/V + | | 5 | 5 | 16 |
| | Appln. | UAN @ 2.5% V/V | Rate | Scale Min-Max | | |
| Trt | Timing | Treatment/Product | a.i. rate | Unit | 0-100 | 0-100 | 0-100 |
|---|---|---|---|---|---|---|---|
| 9 | Post | Mesotrione-Cu | 210(a.e) | GA/Ha | 0 | 0 | 95 |
| 10 | In furrow at seeding | Chlorpyrifos | 11.2 | GA/100 Row M | 0 | 0 | 0 |
| 11 | In furrow at seeding | Chlorpyrifos | 11.2 | GA/100 Row M | 6.3 | 30 | 88.8 |
| | Followed post | Mesotrione | 105 | GA/Ha | | | |
| 12 | In furrow at seeding | Chlorpyrifos | 11.2 | GA/100 Row M | 0 | 0 | 71.3 |
| | Followed post | Mesotrione-Cu + s-metolachlor + benoxacor | 105(a.e) + 1053 + 52.5 | GA/Ha | | | |
| 13 | In furrow at seeding | Chlorpyrifos | 11.2 | GA/100 Row M | 1.3 | 1.3 | 95 |
| | Followed post | Mesotrione-Cu + s-metolachlor + atrazine + benoxacor | 105(a.e) + 1053 + 394 + 52.5 | GA/Ha | | | |
| 14 | In furrow at seeding | Chlorpyrifos | 11.2 | GA/100 Row M | 0 | 0 | 82.5 |
| | Followed post | Mesotrione-Cu | 105(a.e) | GA/Ha | | | |
| 15 | In furrow at seeding | Chlorpyrifos | 11.2 | GA/100 Row M | 15 | 28.8 | 95 |
| | Followed post | Mesotrione | 210 | GA/Ha | | | |
| 16 | In furrow at seeding | Chlorpyrifos | 11.2 | GA/100 Row M | 1.3 | 0 | 93.8 |
| | Followed post | Mesotrione-Cu + s-metolachlor + benoxacor | 210(a.e) + 2105 + 105 | GA/Ha | | | |
| 17 | In furrow at seeding | Chlorpyrifos | 11.2 | GA/100 Row M | 10 | 5 | 95 |
| | Followed post | Mesotrione-Cu + s-metolachlor + atrazine + benoxacor | 210(a.e) + 2100 + 788 + 105 | GA/Ha | | | |
| 18 | In furrow at seeding | Chlorpyrifos | 11.2 | GA/100 Row M | 0.8 | 0 | 95 |
| | Followed post | Mesotrione-Cu | 210(a.e) | GA/Ha | | | |
| 19 | In furrow at seeding | Terbufos | 11.2 | GA/100 Row M | 0 | 0 | 0 |
| 20 | In furrow at seeding | Terbufos | 11.2 | GA/100 Row M | 13.8 | 43.8 | 88.8 |
| | Followed post | Mesotrione | 105 | GA/Ha | | | |
| 21 | In furrow at seeding | Terbufos | 11.2 | GA/100 Row M | 0 | 0 | 73.8 |
| | Followed post | Mesotrione-Cu + s-metolachlor + benoxacor | 105(a.e) + 1053 + 52.5 | GA/Ha | | | |

TABLE I-continued

| | | | | Crop/Variety | | |
|---|---|---|---|---|---|---|
| | | | | Corn 'NK58D1 | Sweet Corn 'Jubilee SS | Weed/ *Amaranthus retroflexus* |
| | | | | Rating Data Type | | |
| | | | | Phytotox. | Phytotox. | Weed Control |
| | | | | Rating Unit Scale | | |
| | | | | % | % | % |
| | | All post applications with: | | Evaluation @ Days after last application | | |
| | | COC @ 1% V/V + | | 5 | 5 | 16 |
| | Appln. | UAN @ 2.5% V/V | Rate | Scale Min-Max | | |
| Trt | Timing | Treatment/Product | a.i. rate | Unit | 0-100 | 0-100 | 0-100 |
| 22 | In furrow at seeding | Terbufos | 11.2 | GA/100 Row M | 2.5 | 0 | 93.8 |
| | Followed post | Mesotrione-Cu + s-metolachlor + atrazine + benoxacor | 105(a.e) + 1053 + 394 + 52.5 | GA/Ha | | | |
| 23 | In furrow at seeding | Terbufos | 11.2 | GA/100 Row M | 0 | 0 | 83.8 |
| | Followed post | Mesotrione-Cu | 105(a.e) | GA/Ha | | | |
| 24 | In furrow at seeding | Terbufos | 11.2 | GA/100 Row M | 26.3 | 43.8 | 95 |
| | Followed post | Mesotrione | 210 | GA/Ha | | | |
| 25 | In furrow at seeding | Terbufos | 11.2 | GA/100 Row M | 2 | 0 | 76.3 |
| | Followed post | Mesotrione-Cu + s-metolachlor + benoxacor | 210(a.e) + 2105 + 105 | GA/Ha | | | |
| 26 | In furrow at seeding | Terbufos | 11.2 | GA/100 Row M | 7.5 | 7.5 | 95 |
| | Followed post | Mesotrione-Cu + s-metolachlor + atrazine + benoxacor | 210(a.e) + 2100 + 788 + 105 | GA/Ha | | | |
| 27 | In furrow at seeding | Terbufos | 11.2 | GA/100 Row M | 1.3 | 0 | 95 |
| | Followed post | Mesotrione-Cu | 210(a.e) | GA/Ha | | | |
| 28 | Post | Chlorpyrifos | 1120 | GA/Ha | 0 | 0 | 0 |
| 29 | Post tank mix/foliar | Chlorpyrifos | 1120 | GA/Ha | 4603 | 61.3 | 95 |
| | | Mesotrione | 105 | GA/Ha | | | |
| 30 | Post tankmix/foliar | Chlorpyrifos | 1120 | GA/Ha | 3.8 | 2.5 | 81.3 |
| | | Mesotrione-Cu + s-metolachlor + benoxacor | 105(a.e) + 1053 + 52.5 | GA/Ha | | | |
| 31 | Post tankmix/foliar | Chlorpyrifos | 1120 | GA/Ha | 7 | 8.8 | 93.8 |
| | | Mesotrione-Cu + s-metolachlor + atrazine + benoxacor | 105(a.e) + 1050 + 394 + 52.5 | GA/Ha | | | |
| 32 | Post tankmix/foliar | Chlorpyrifos | 1120 | GA/Ha | 5 | 8.8 | 91.3 |
| | | Mesotrione-Cu | 105(a.e) | GA/Ha | | | |
| 33 | Post tankmix/foliar | Chlorpyrifos | 1120 | GA/Ha | 70 | 75 | 92.5 |
| | | Mesotrione | 210 | GA/Ha | | | |
| 34 | Post tankmix/foliar | Chlorpyrifos | 1120 | GA/Ha | 8.8 | 3.3 | 93.8 |
| | | Mesotrione-Cu + s-metolachlor + benoxacor | 210(a.e) + 2105 + 105 | GA/Ha | | | |
| 35 | Post tankmix/ | Chlorpyrifos | 1120 | GA/Ha | 20 | 10 | 95 |

TABLE I-continued

| | | | | | Crop/Variety | | |
|---|---|---|---|---|---|---|---|
| | | | | | Corn 'NK58D1' | Sweet Corn 'Jubilee SS' | Weed/ *Amaranthus retroflexus* |
| | | | | | Rating Data Type | | |
| | | | | | Phytotox. | Phytotox. | Weed Control |
| | | | | | Rating Unit Scale | | |
| | | All post applications with: | | | % Evaluation @ Days after last application | | |
| | | COC @ 1% V/V + | | | 5 | 5 | 16 |
| | Appln. | UAN @ 2.5% V/V | | Rate | Scale Min-Max | | |
| Trt | Timing | Treatment/Product | a.i. rate | Unit | 0-100 | 0-100 | 0-100 |
| | foliar | Mesotrione-Cu + s-metolachlor + atrazine + benoxacor | 210(a.e) + 2100 + 788 + 105 | GA/Ha | | | |
| 36 | Post tankmix/ | Chlorpyrifos | 1120 | GA/Ha | 8.8 | 12.5 | 95 |
| | foliar | Mesotrione-Cu | 210(a.e) | GA/Ha | | | |

EXAMPLE 2

Insecticide Pre-Plant Incorporated Followed by Post Application of the Herbicide Prior to the planting of corn and weed, the substrate was filled into plastic pots and the different insecticides were applied with glasshouse spray equipment on bare soil at rates indicated in the results table. After the insecticide application, the substrate in the pots was mixed up in order to get an even distribution of the insecticide throughout the pot Crop and weed were planted following this procedure and grown under standard glasshouse conditions allowing optimal plant growth until 2-3 leaf stage. Then the herbicides were applied according to the rates indicated in the results table post emergent foliar over the top including standard adjuvants. The plants were visually evaluated on a scale of 0-100% wherein 0% indicated no phytotoxicity and 100% indicated full control or death. 0-15% indicates acceptable crop tolerance, 85-100% acceptable weed control. The evaluation was done at the time when maximal phytotoxicity or activity occurred. The results are shown in Table 2.

TABLE 2

| | | | | Crop/Variety | |
|---|---|---|---|---|---|
| | | | | Corn Cecilia | Weed/ *Solanum Nigrum* |
| | | | | Rating Data Type | |
| | | | | Phytotox. | Weed Control |
| | | | | Rating Unit Scale | |
| | | All post applications with: | | % Evaluation @ Days after last application | |
| | | | | 20 | 43 |
| | Appln. | COC @ 1% V/V + UAN @ 2.5% V/V | a.i. rate/ | Scale Min-Max | |
| Trt | Timing | Treatment/Product | GA/Ha | 0-100 | 0-100 |
| 1 | Post | Mesotrione | 400 | 0 | 0 |
| | | | 200 | 0 | 100 |

TABLE 2-continued

| | | | | Crop/Variety | |
|---|---|---|---|---|---|
| | | | | Corn Cecilia | Weed/ *Solanum Nigrum* |
| | | | | Rating Data Type | |
| | | | | Phytotox. | Weed Control |
| | | | | Rating Unit Scale | |
| | | All post applications with: | | % Evaluation @ Days after last application | |
| | | | | 20 | 43 |
| | Appln. | COC @ 1% V/V + UAN @ 2.5% V/V | a.i. rate/ | Scale Min-Max | |
| Trt | Timing | Treatment/Product | GA/Ha | 0-100 | 0-100 |
| | | | 100 | 5 | 98 |
| 2 | Post | Mesotrione-Cu | 400 | 0 | 100 |
| | | | 200 | 0 | 95 |
| | | | 100 | 5 | 95 |
| 3 | Pre-plant incorporated | Chlorpyrifos-methyl | 1000 | | |
| | Post | Mesotrione | 400 | 30 | 100 |
| | | | 200 | 20 | 100 |
| | | | 100 | 20 | 98 |
| 4 | Pre-plant incorporated | Chlorpyrifos-methyl | 1000 | | |
| | Post | Mesotrione-Cu | 400 | 0 | 100 |
| | | | 200 | 0 | 100 |
| | | | 100 | 0 | 100 |
| 5 | Pre-plant incorporated | Terbufos | 1000 | | |
| | Post | Mesotrione | 400 | 30 | 100 |
| | | | 200 | 30 | 100 |
| | | | 100 | 20 | 100 |
| 6 | Pre-plant incorporated | Terbufos | 1000 | | |
| | Post | Mesotrione-Cu | 400 | 0 | 100 |
| | | | 200 | 0 | 100 |
| | | | 100 | 0 | 98 |

TABLE 2-continued

| | | | Crop/Variety | |
| | | | Corn Cecilia | Weed/ *Solanum Nigrum* |
| | | | Rating Data Type | |
| | | | Phytotox. Rating Unit Scale | Weed Control Scale |
| | All post applications with: | | % Evaluation @ Days after last application | |
| | COC @ 1% V/V + | a.i. rate/ | 20 | 43 |
| Appln. | UAN @ 2.5% V/V | | Scale Min-Max | |
| Trt Timing | Treatment/Product | GA/Ha | 0-100 | 0-100 |
| 7 Pre-plant incorporated | Tefluthrin | 1000 | | |
| Post | Mesotrione | 400 | 30 | 100 |
| | | 200 | 30 | 100 |
| | | 100 | 25 | 98 |
| 8 Pre-plant incorporated | Tefluthrin | 1000 | | |
| Post | Mesotrione-Cu | 400 | 0 | 100 |
| | | 200 | 0 | 100 |
| | | 100 | 0 | 100 |
| 9 Pre-plant incorporated | Thiamethoxam | 1000 | | |
| Post | Mesotrione | 400 | 30 | 100 |
| | | 200 | 30 | 95 |
| | | 100 | 20 | 100 |
| 10 Pre-plant incorporated | Thiamethoxam | 1000 | | |
| Post | Mesotrione-Cu | 400 | 0 | 100 |
| | | 200 | 0 | 100 |
| | | 100 | 0 | 100 |
| 11 Post | (ICb) | 200 | 25 | 98 |
| | | 100 | 5 | 98 |
| | | 50 | 5 | 98 |
| 12 Post | (ICb)-Cu | 200 | 0 | 85 |
| | | 100 | 0 | 90 |
| | | 50 | 5 | 85 |
| 13 Pre-plant incorporated | Chlorpyrifos-methyl | 1000 | | |
| Post | (ICb) | 200 | 40 | 100 |
| | | 100 | 30 | 100 |
| | | 50 | 20 | 100 |
| 14 Pre-plant incorporated | Chlorpyrifos-methyl | 1000 | | |
| Post | (ICb)-Cu | 200 | 5 | 100 |
| | | 100 | 5 | 98 |
| | | 50 | 0 | 98 |
| 15 Pre-plant incorporated | Terbufos | 1000 | | |
| Post | (ICb) | 200 | 40 | 100 |
| | | 100 | 40 | 100 |
| | | 50 | 20 | 95 |
| 16 Pre-plant incorporated | Terbufos | 1000 | | |
| Post | (ICb)-Cu | 200 | 10 | 90 |
| | | 100 | 5 | 100 |
| | | 50 | 5 | 100 |
| 17 Pre-plant incorporated | Tefluthrin | 1000 | | |
| Post | (ICb) | 200 | 40 | 100 |
| | | 100 | 40 | 100 |
| | | 50 | 20 | 100 |
| 18 Pre-plant incorporated | Tefluthrin | 1000 | | |
| Post | (ICb)-Cu | 200 | 0 | 100 |
| | | 100 | 0 | 100 |
| | | 50 | 10 | 95 |
| 19 Pre-plant incorporated | Thiamethoxam | 1000 | | |
| Post | (ICb) | 200 | 30 | 100 |
| | | 100 | 30 | 100 |
| | | 50 | 20 | 100 |
| 20 Pre-plant incorporated | Thiamethoxam | 1000 | | |
| Post | (ICb)-Cu | 200 | 5 | 100 |
| | | 100 | 0 | 90 |
| | | 50 | 0 | 90 |

EXAMPLE 3

Insecticide and Herbicide Applied Tank-Mixed Post Emergent

Prior to the planting of corn and weed, the substrate was filled into plastic pots. Crop and weed were planted following this procedure and grown under standard glasshouse conditions allowing optimal plant growth until 2-3 leaf stage. Then the herbicides were applied according the rates indicated in the results table post emergent foliar over the top including standard adjuvants. The plants were visually evaluated on a scale of 0-100% wherein 0% indicated no phytotoxicity and 100% indicated full control or death. 0-15% indicates acceptable crop tolerance, 85-100% acceptable weed control. The evaluation was done at the time when maximal phytotoxicity or activity occurred. The results are shown in Table 3.

TABLE 3

| | | | Crop/Variety | |
| | | | Corn Sweet honeycomb | Weed/ *Solanum Nigrum* |
| | | | Rating Data Type | |
| | | | Phytotox. Rating Unit Scale | Weed Control Scale |
| | | | % Evaluation @ Days after last application | |
| | | a.i. rate/ | 8 | 34 |
| Appln. | | | Scale Min-Max | |
| Trt Timing | Treatment/Product | GA/Ha | 0-100 | 0-100 |
| 1 Post | Mesotrione | 400 | 20 | 100 |
| | | 200 | 20 | 100 |
| | | 100 | 10 | 100 |

TABLE 3-continued

| | | | | Crop/Variety | |
|---|---|---|---|---|---|
| | | | | Corn Sweet honeycomb | Weed/ *Solanum Nigrum* |
| | | | | Rating Data Type | |
| | | | | Phytotox. | Weed Control |
| | | | | Rating Unit Scale | |
| | | | | % | % |
| | | | | Evaluation @ Days after last application | |
| | Appln. | | a.i. rate/ | 8 | 34 |
| | | | | Scale Min-Max | |
| Trt | Timing | Treatment/Product | GA/Ha | 0-100 | 0-100 |
| 2 | Post | Mesotrione-Cu | 400 | 0 | 100 |
| | | | 200 | 0 | 100 |
| | | | 100 | 0 | 95 |
| 3 | Post | Chlorpyrifos-methyl | 1000 | | |
| | | Mesotrione | 400 | 100 | 100 |
| | | | 200 | 90 | 100 |
| | | | 100 | 85 | 100 |
| 4 | Post | Chlorpyrifos-methyl | 1000 | | |
| | | Mesotrione-Cu | 400 | 10 | 100 |
| | | | 200 | 0 | 95 |
| | | | 100 | 0 | 100 |
| 5 | Post | Terbufos | 1000 | | |
| | | Mesotrione | 400 | 50 | 100 |
| | | | 200 | 30 | 100 |
| | | | 100 | 15 | 100 |
| 6 | Post | Terbufos | 1000 | | |
| | | Mesotrione-Cu | 400 | 0 | 100 |
| | | | 200 | 0 | 100 |
| | | | 100 | 0 | 100 |
| 7 | Post | Tefluthrin | 100 | | |
| | | Mesotrione | 400 | 30 | 100 |
| | | | 200 | 20 | 100 |
| | | | 100 | 20 | 100 |
| 8 | Post | Tefluthrin | 100 | | |
| | | Mesotrione-Cu | 400 | 0 | 100 |
| | | | 200 | 0 | 100 |
| | | | 100 | 0 | 100 |
| 9 | Post | Thiamethoxam | 70 | | |
| | | Mesotrione | 400 | 25 | 100 |
| | | | 200 | 20 | 100 |
| | | | 100 | 10 | 100 |
| 10 | Post | Thiamethoxam | 70 | | |
| | | Mesotrione-Cu | 400 | 0 | 100 |
| | | | 200 | 0 | 100 |
| | | | 100 | 0 | 100 |

We claim:

1. A pesticidally active combination comprising mesotrione copper salt and an insecticide selected from the group consisting of chlorpyrifos-methyl, terbufos, tefluthrin and thiamethoxam.

2. A pesticidally active combination according to claim 1, wherein the agrochemically acceptable salt is formed using metal chelates.

3. A pesticidally active combination according to claim 1, which comprises one or more additional active ingredients.

4. A pesticidally active combination according to claim 3, wherein the one or more additional active ingredients are herbicides and/or safeners.

5. A pesticidally active combination according to claim 3, wherein the one or more additional active ingredients are selected from the group consisting of atrazine, terbuthylazine, metolachlor, s-metolachlor, benoxacor, furilazole, dichlormid, flurazole acetochlor, p-dimethenamid, glyphosate, cloquintocet, fluxofenim, nicosulfuron, rimsulfuron, foramsulfuron, isoxadifene, prosulfuron, primisulfuron, dicamba, trifloxysulfuron.

6. A method of controlling undesired plant growth in crops of useful plants, said method comprising the application of the pesticidally active combination of claim 1.

7. A pesticidally active pre-mix composition comprising mesotrione copper salt and an insecticide selected from the group consisting of chlorpyrifos-methyl, terbufos, tefluthrin and thiamethoxam.

* * * * *